United States Patent [19]

Thiem et al.

[11] 4,031,116

[45] June 21, 1977

[54] PROCESS FOR PREPARING PURE 1-NITROANTHRAQUINONE

[75] Inventors: Karl-Werner Thiem, Cologne; Wolfgang Auge, Odenthal; Rütger Neeff, Leverkusen, all of Germany

[73] Assignee: Bayer Aktiengesellschaft, Leverkusen, Germany

[22] Filed: July 20, 1976

[21] Appl. No.: 707,130

Related U.S. Application Data

[63] Continuation of Ser. No. 499,734, Aug. 22, 1974, abandoned.

[30] Foreign Application Priority Data

Aug. 31, 1973 Germany ........................ 2343978

[52] U.S. Cl. .............................................. 260/369
[51] Int. Cl.$^2$ .......................................... C07C 76/00
[58] Field of Search ................................. 260/369

[56] References Cited

UNITED STATES PATENTS

| | | | |
|---|---|---|---|
| 2,874,168 | 2/1959 | Graham et al. | 260/369 |
| 3,798,243 | 3/1974 | Toth | 260/369 |
| 3,836,601 | 9/1974 | Frey et al. | 260/364 |

FOREIGN PATENTS OR APPLICATIONS 2,252,013   5/1937   Germany

OTHER PUBLICATIONS

Houben Das Anthracene und das Anthrachinone, George Thiem, Verlag, Liepzig, 1929, p. 284.

*Primary Examiner*—Arthur P. Demers
*Attorney, Agent, or Firm*—Burgess, Dinklage & Sprung

[57] ABSTRACT

Pure 1-nitroanthraquinone substantially free of dinitroanthraquinone is prepared by:
1. Nitrating anthraquinone or a mixture which contains anthraquinone with at least 90% nitric acid at a temperature of at least 0° C wherein the mole ratio of nitric acid to anthraquinone is less than 20 to 1;
2. Stopping the reaction when the anthraquinone conversion is at least 50% by cooling the reaction mixture to a temperature of at most 20° C and/or by adjusting the mole fraction of nitric acid in the reaction mixture to a value of at most 0.86;
3. Precipitating 1-nitroanthraquinone by adjusting the mole fraction of nitric acid to a value of from 0.7 to 0.4 and/or by reducing the temperature to at most 20° C; and
4. Separating the precipitated 1-nitroanthraquinone and subjecting it to vacuum distillation.

19 Claims, No Drawings

PROCESS FOR PREPARING PURE 1-NITROANTHRAQUINONE

This is a continuation of application Ser. No. 499,734, filed Aug. 22, 1974, now abandoned.

BACKGROUND

This invention relates to a process for preparing 1-nitroanthraquinone substantially free of dinitroanthraquinone.

In the processes hitherto known for producing 1-nitroanthraquinone from anthraquinone and nitric acid, nitration and purification of the resulting 1-nitroanthraquinone have proved very difficult.

Either the products obtained are not pure enough for conversion into dye intermediate products or the yield of pure product is so low as to render the process uneconomical. Thus, for example German Offenlegungsschrift No. 2,162,538 claims the nitration of anthraquinone in nitric acid with a mole ratio of at least 20, in particular from 24 to 50. (The term "mole ratio" is used herein to denote the ratio of nitric acid to anthraquinone or anthraquinone plus nitration products.)

The reaction is stopped by the addition of considerable quantities of water, with the result that the product obtained is purified by the dilute nitric acid thereby formed. The substances which go into solution, apart from a small quantity of 1-nitroanthraquinone, are mainly 2-nitroanthraquinone, anthraquinone and 1,6- and 1,7-dinitroanthraquinone. Approximately 92% pure 1-nitroanthraquinone has been obtained by this method in a maximum yield of 74.5%. (All percentages herein are by weight unless otherwise stated.)

Since the dilute nitric acid formed must be worked up and in some cases regenerated, it is a serious economic disadvantage to have to stop the reaction with a large quantity of water. For this reason, German Offenlegungsschrift No. 2,227,340 claims so-called nitration inhibitors, such as nitrites, phosphates or phosphoric acid, which are intended to reduce the reaction velocity. The disadvantage of this method is that it introduces foreign substances into the reaction mixture so that a separate operation is required to work up the nitric acid.

Another possibility for stopping the nitration of anthraquinone with excess nitric acid has been described in German Offenlegungsschrift No. 2,220,377.

To regulate (reduce) the reaction velocity, the process described uses nitric acid diluted only to such a degree that, at the end of the nitration reaction, the total nitric acid content of the mixture is still above the azeotropic limit (68% nitric acid). Whereas nitric acid which has a concentration of at least 93%, and preferably 97%, is used for nitration and a mole ratio of from 20 to 120 is employed, the nitric acid used to reduce the nitration velocity is preferably at a concentration of from 70 to 80%, so that when nitration is terminated the nitric acid content of the nitration mixture is preferably from 75 to 90%.

The resulting reaction mixture is separated into nitration products and two nitric acid fractions. If desired, the crystallised nitration product may first be separated and the remaining nitric acid fractionated, or alternatively a highly concentrated nitric acid may first be removed from the reaction mixture and the remaining mixture may then be divided into nitration product and dilute acid. The concentrated nitric acid should then be used again for subsequent nitration reactions and the dilute nitric acid for regulating the reaction velocity.

The relatively large quantities of dilute nitric acid obtained by this operation result in a purer 1-nitroanthraquinone obtained by nitration because the major portion of the reaction by-products and the unreacted anthraquinone (with the exception of 1,5- and 1,8-dinitroanthraquinone) are dissolved in the dilute nitric acid while the 1-nitroanthraquinone crystallises. The disadvantages of this process lie in the fact that complete or partial purification of this dilute acid is necessary if the acid is to be used again to stop the reaction and hence act as a purifying agent to obtain a reasonably pure 1-nitroanthraquinone.

The quantities of nitric acid which have to be handled are enormous. If, for example, nitration is carried out with a mole ratio of about 38 to 40:1 and the reaction is stopped with 74–78.5% nitric acid, then the mole ratio after stopping the reaction is 78 to 100:1 (the proportion by weight of the resulting 78 to 87% nitric acid to anthraquinone plus nitroanthraquinone derivatives being approximately 22 to 37:1).

In spite of these enormous efforts, the 1-nitroanthraquinone obtained is at the most 91% pure and the yield is approximately 65%. The product still contains substantial quantities of anthraquinone, 1,5-dinitroanthraquinone and 1,8-dinitroanthraquinone and cannot be used directly for the production of dye intermediate products without further purification.

Thus, for example, German Offenlegungsschrift No. 2,206,960 describes the treatment of partly purified products which contain dinitroanthraquinone with aqueous $Na_2SO_3$ solution in the presence of sodium hydroxide solution. The 1-nitroanthraquinone obtained by this method also has a maximum purity of only 97% (the remainder consisting of 1,5- and 1,8-dinitroanthraquinone). In addition to 2-nitroanthraquinone and part of the dinitroanthraquinones, about 5% of 1-nitroanthraquinone enter the aqueous filtrate in the form of intensively coloured water-soluble compounds, and, together with the inorganic sulphur compounds, they heavily contaminate the effluent water.

Other methods for completely separating the by-products of nitration, e.g., washing with acid amides (German Offenlegungschrift No. 2,039,822) or treatment with saturated chlorinated hydrocarbons which contain nitric acid (German Offenlegungsschrift No. 2,142,100) result in 1-nitroanthraquinone which is only 95–96% pure (with a total yield via nitration and purification of 42 to 43%).

No process has hitherto been described by means of which a very pure 1-nitroanthraquinone, almost free from dinitroanthraquinone, can be obtained in economical yields.

It has now surprisingly been found that very pure 1-nitroanthraquinone, which is almost free from dinitroanthraquinone and which can be used directly for the preparation of dye intermediate products, can be prepared without producing large quantities of dilute nitric acid, with the result that the nitration process can be rendered much more economical and much time, energy and expenditure of apparatus can be saved. In this process, anthraquinone or a mixture which contains anthraquinone is nitrated in the presence of highly concentrated nitric acid, in particular in >90% nitric acid, with a mole ratio of nitric acid to anthraquinone of <20:1 and at a temperature of ≥ 0° C, in particular ≥ 45° C; and the reaction is stopped by cooling the reaction mixture to temperatures below 30° C and/or by lowering the mole fraction of nitric acid e.g., by the addition of diluents such as water and/or by distilling off nitric acid; the 1-nitroanthraquinone is precipitated, either by further cooling of the reaction mixture and/or by further reducing of the mole fraction of nitric acid, e.g., by the addition of diluents such as water and/or dilute nitric acid, in particular <90% nitric acid and/or by further removal of nitric acid by distillation; and the precipitate is isolated and freed from nitric acid, in particular by vacuum drying, and finally subjected to vacuum rectification.

In the text which follows, the term "mole fraction" is used herein to denote the mole fraction of nitric acid in a given total mixture in accordance with the following equation:

$$\gamma_{HNO_3} = n_{HNO_3}/(n_{HNO_3} + n_{N_2} + n_{H_2O})$$

where
$n$ = number of moles, and
N = nitroanthraquinone derivatives and anthraquinone.

The process according to the invention is characterised in that anthraquinone or a mixture which contains anthraquinone is nitrated with at least 90%, and in particular 95-100%, nitric acid at temperatures of at least 0° C, in particular ⩾ 45° C, preferably 55°-75° C, and with a mole ratio of nitric acid to anthraquinone of <20:1, in particular 6:1 to 15:1; the reaction is stopped when the anthraquinone conversion is ⩾ 50%, in particular 80 to 100%, by cooling the reaction mixture to temperatures ⩽ 30° C and/or by adjusting the mole fraction of nitric acid to a value ⩽ 0.86, for example by the addition of water and/or removal of nitric acid by distillation; 1-nitroanthraquinone is thereafter precipitated by adjusting the mole fraction of nitric acid to a value of from 0.7 to 0.4 by distilling off nitric acid and/or by diluting with water and/or by adding dilute nitric acid, and/or the 1-nitroanthraquinone is precipitated by lowering the temperature to ⩽ 20° C; and the precipitated 1-nitroanthraquinone is separated off and subjected to vacuum distillation, optionally in the presence of solvents which are stable under the conditions of distillation, which are inert towards nitroanthraquinone and which boil at temperatures between 100° and 350° C.

By mixtures which contain anthraquinone are meant mixtures which, in addition to anthraquinone, contain nitroderivatives of anthraquinone such as 1-nitroanthraquinone, 2-nitroanthraquinone and di-nitroanthraquinone.

The relative proportion of anthraquinone to nitrocompounds of anthraquinone in such mixtures is not critical for the process according to the invention, but mixtures containing at least 50% by weight of anthraquinone are normally used.

The process of nitration according to the invention can be carried out in conventional reaction apparatus such as flow tubes, tank cascades or separate tanks, either continuously or discontinuously. In order to obtain maximum possible yields of 1-nitroanthraquinone in continuous processes, the flow, if flow tubes are used, should be a distinct plug flow and Reynolds numbers should be ⩾ 2300; if cascades or tanks are used, an ideal spectrum of residence times in the apparatus should be achieved. The reaction is preferably carried out adiabatically or partly adiabatically but may, of course, also be carried out isothermally.

When nitration is carried out with mole ratios of nitric acid to anthraquinone of from 6:1 to 19:1, for example using 99% nitric acid, mole fractions of $\gamma_{HNO_3}$ = 0.69 to 0.87 become established. The point at which the reaction is stopped depends on the mole fraction of nitric acid in the mixture and of course also on the temperature. The reaction mixture must be adjusted to lower mole fractions at higher temperatures than at low temperatures.

If, for example, nitration is carried out with a mole ratio of 19:1, 15:1, 10:1 or 6:1, the reaction may be stopped by cooling to temperatures of ⩽ −5° C, ⩽ 5° C, ⩽ 15° C or ⩽ 30° C respectively. The corresponding mole fractions are $\gamma_{HNO_3}$ = 0.871; 0.847; 0.793 or 0.694. The appropriate mole fractions may, of course, also obtained by stopping the reaction by rapidly distilling off concentrated nitric acid. At higher temperatures, the reaction mixture, must, of course, be adjusted to lower mole fractions. Thus, for example, at 65° C (45° C, 25° C) and mole ratios of 18:1, 10:1 and 5:1, the appropriate acid concentrations are about 86% (90; 93), 91.5% (93.5; 95.5) and 95.5% (96.5; 97.5) and the appropriate mole fractions are 0.615 (0.692; 0.758); 0.702 (0.744; 0.791) and 0.733 (0.754; 0.775). These values can easily be obtained if water is added to the reaction mixture to stop the reaction.

In the same way as the stopping of the reactions, the purification by crystallisation is also dependent upon the temperature and the mole fraction of nitric acid in the nitration mixture. Since nitric acid has a relatively high vapour pressure at elevated temperature, it would appear more suitable to filter off the crystallisate at room temperature or temperatures of up to 30° C. The quantities and concentrations of nitric acid required for purification depend upon which impurities are to be separated and in what quantities. If, for example, 10% by weight (5% by weight) of anthraquinone is to be removed from the nitroanthraquinone mixture, then the acid concentrations may be adjusted, for example, to about 93% (82%), 84% (78%), 80% (76%) or 76% (72%) and the mole fractions accordingly to $\gamma_{HNO_3}$ = 0.69 (0.53), 0.58 (0.49), 0.52 (0.47) or 0.46 (0.42).

The same applies, of course, to the separation of 2-nitroanthraquinone from nitroanthraquinone mixtures. If, for example, about 8% by weight of 2-nitroanthraquinone and less than 3% by weight of anthraquinone are to be separated, then the mole fractions must be adjusted to $\gamma_{HNO_3}$ = 0.51; 0.49; 0.47 or 0.42 if the acid concentrations are about 80%, 78%, 76% or 72%. In order to keep the loss of 1-nitroanthraquinone by separation as small as possible, the mole fractions should be large (small), i.e., the mole ratios small (large), when the acid concentrations are high (low).

The larger the quantity of appropriately diluted nitric acid, the smaller is the loss of 1-nitroanthraquinone by separation, but large quantities of dilute nitric acid are uneconomical because the nitric acid must then be distilled and in some cases reconcentrated. It has now been found that 1-nitroanthraquinone sufficiently pure for the next stage of the process is obtained by using 90-72% nitric acid for the process of crystallisation and the purification associated with it, and by adjusting the mole fractions accordingly to values between $\gamma_{HNO_3}$ = 0.70 and $\gamma_{HNO_3}$ = 0.42.

The following possible combinations can be employed for stopping the reaction and for subsequent purification in the process according to the invention.

If the reaction is stopped by the addition of a small quantity of water and/or by distilling off nitric acid and/or by cooling the reaction mixture, the required mole fraction for precipitation of 1-nitroanthraquinone can be adjusted by adding water and/or dilute nitric acid and/or by distilling off nitric acid.

If a mole ratio of nitration products and unreacted anthraquinone to nitric acid of ≤ 12:1 is obtained by distilling off nitric acid, or if nitration is carried out with these mole ratios, then 1-nitroanthraquinone precipitated at temperatures of up to 15° C can be separated from the by-products in the filtrate. These by-products can be precipitated almost completely from the filtrate if the mole fraction is adjusted to a value of ≤ 0.4, e.g., by dilution with water or by partial or complete removal of nitric acid by distillation. This precipitated mixture of by-products which is removed in the usual manner contains almost all the 2-nitroanthraquinone. This can be isolated in a relatively pure form by carrying out the aforesaid precipitation as a fractional precipitation. Nitric acid free from organic products can be returned to the process, for example after reconcentrating it, or as a diluent.

1-Nitroanthraquinone precipitated from nitric acid is obtained in a crystalline form and can be filtered off relatively easily (e.g. by means of a rotary, plane or pressure filter). The filter cake, after having been briefly washed with dilute nitric acid, may be washed until neutral with water in the usual manner and dried, or it may be directly freed from nitric acid in a vacuum (e.g., using a flow drier or roller drier). The dried 1-nitroanthraquinone is then subjected to vacuum distillation, in particular rectification.

The temperatures and pressures given below indicate the conditions at the head of the distillation apparatus.

Distillation may be carried out at a temperature of 200°–400° C and 0.5 to 100 Torr, preferably 235–330° C and 1.5 to 50 Torr, in particular at 245°–315° C and 2.5 to 35 Torr. It has been found particularly suitable to carry out the distillation at temperatures of between 265° and 300° C and under a vacuum of 5 to 20 Torr. The whole process may be carried out continuously or discontinuously.

According to one particular variation, the already partly purified product and a solvent which boils at a temperature of 100° to 350° C, which is stable under the distillation conditions and which is inert towards the product, for example high boiling hydrocarbons or silicone oils, are distilled off together under the conditions indicated above, and in particular at 200° to 350° C and 0.5 to 100 Torr. 1-Nitroanthraquinone which crystallises from the condensate is then removed by conventional methods.

The process according to the invention may, for example, be carried out according to the following variations:

Variation 1

Nitration is stopped by transferring the whole reaction mixture to an evaporator, e.g., a thin layer contact evaporator or a falling film evaporator, and distilling off the required proportion of nitric acid, preferably rapidly. The mixture is then transferred from the sump to a crystallising apparatus in which 1-nitroanthraquinone is precipitated, by cooling the mixture to temperatures of up to 15° C and/or by adding water or dilute nitric acid, and the precipitate is then separated in a separating device. The by-products dissolved in the filtrate can be precipitated by diluting the filtrate with water or by distilling off nitric acid. The nitric acid freed from organic products can be separated into a high-percentage nitric acid and a low-percentage nitric acid by means of a separating column. The high-percentage acid may be returned to the nitration process and the low-percentage acid may be used for the crystallisation step.

The precipitated 1-nitroanthraquinone is freed from nitric acid, in particular by direct vacuum drying, and subjected to high vacuum rectification.

Variation 2

Nitration is stopped in a cooling apparatus by cooling to the appropriate temperatures of up to 25° C, depending on the mole ratios. 1-Nitroanthraquinone is then precipitated by diluting the reaction mixture with water and/or dilute nitric acid and/or by cooling the reaction mixture to 15° C or lower, and it is then separated in a separating device. Further purification of the 1-nitroanthraquinone and working up of the filtrate are carried out as in Variation 1.

Variation 3

Nitration is stopped by adding a little water to the reaction mixture in a mixing vessel. The reaction mixture is then adjusted to a mole fraction of ≤ 0.7 by the addition of dilute nitric acid or further quantities of water and/or by distilling off the appropriate quantities of nitric acid. The precipitated 1-nitroanthraquinone is separated. Further purification of the 1-nitroanthraquinone and working up of the filtrate are carried out as described in Variation 1. Combinations of these variations are, of course, also possible.

The advantages of the process according to the invention lie in the fact that nitration can be stopped with small mole ratios ( ≤ 19:1) by a relatively slight alteration of the conditions (e.g., temperature or mole fraction of nitric acid).

The quantities of nitric acid required for crystallisation and the associated purification are also small so that the cost of redistillation and, if indicated, regeneration of nitric acid are not a substantial burden on the process. Moreover, the process provides high yields of pure 1-nitroanthraquinone which is practically free from dinitroanthraquinone and can be used directly for the production of dyes. Another advantage of this process is that all the by-products of nitration can be isolated, if necessary by additional operations, and worked up. Thus, for example, the sump product of high vacuum rectification, which substantially contains only 1-nitroanthraquinone and 1,5- and 1,8-dinitroanthraquinone, can be renitrated, e.g., in concentrated nitric acid, to give a mixture of 1,5- and 1,8-dinitroanthraquinone from which 1,5- and 1,8-dinitroanthraquinone can be isolated in a practically pure form by measures similar to those described for the isolation of 1-nitroanthraquinone (fractional precipitation from nitric acid).

In the following examples, the term "mole ratio" always refers to the ratio of nitric acid to anthraquinone or anthraquinone plus nitration products. Unless otherwise indicated, the crystallised product is separated at room temperature. The yield is always based on the quantity of anthraquinone put into the process.

Degrees are given in °C. All the batchwise processes described here can, of course, also be carried out continuously, and vice versa.

EXAMPLE 1

A mixture of 2.08 kg of anthraquinone and 9.545 kg of 99% nitric acid per hour (mole ratio 15:1) cooled to 0° is continuously reacted in a flow tube reactor at a temperature of 55° and with a residence time of 10 minutes. To stop the reaction, the reaction mixture is transferred to an evaporator (e.g. thin layer, circulating or falling film evaporator) immediately on leaving the reactor. In this evaporator, 4.725 kg per hour of 99% nitric acid are distilled off under vacuum (acid concentration about 94.7%, $\gamma_{HNO_3} = 0.740$). The nitric acid distilled off is used again for nitration while the sump product is transferred to a crystallisation vessel into which 5.986 kg per hour of 70% nitric acid are introduced (crystallisation acid 80%, $\gamma_{HNO_3} = 0.519$). The crystallised product is separated by means of a centrifuge (e.g., also by means of a rotary, plane or pressure filter). It is then briefly washed with 75% nitric acid, freed from nitric acid under vacuum, melted, and subjected to vacuum rectification at 10 Torr and a head temperature of 281° C. The yield of 99.2% pure product is 1.683 kg per hour (66% of the theoretical amount). Organic constituents still dissolved in the mother liquor are precipitated by distilling off nitric acid and are separated. The nitric acid is separated by distillation into 99% nitric acid and 70% nitric acid. The 99% acid may be used for nitration, while the 70% acid may be used for crystallisation or may be reconcentrated.

EXAMPLE 2

208 g of anthraquinone and 509 g of 99% nitric acid (more ratio 8:1) are heated to 60° C for 1 hour with stirring. The reaction mixture is then rapidly cooled to 0° C, and 1584 g of 73% nitric acid are added (crystallisation acid 78%, $\gamma_{HNO_3} = 0.493$). The crystallised product is filtered off, washed with a little 76% nitric acid, freed from nitric acid under vacuum and fractionally distilled at 15 Torr and a head temperature of 292°. 157 g of 98.5% 1-nitroanthraquinone are obtained (61.2% of theoretical amount).

EXAMPLE 3

208 g of anthraquinone are introduced into 955 g of 99% nitric acid at 0° with stirring (mole ratio 15:1). The temperature of the reaction mixture rises to 55° in about 6 minutes. This temperature is maintained by cooling until the total reaction time is 10 minutes. 316 g of 99% nitric acid ($\gamma_{HNO_3} = 0.791$) are then distilled off very rapidly at this temperature under vacuum. 100 ml of water are then slowly added to the sump product (crystallisation acid 82%, $\gamma_{HNO_3} = 0.532$). The precipitated product is suction-filtered, washed with a little 75% nitric acid and then with water, dried and subjected to fractional vacuum distillation at 10 Torr and a head temperature of 281°. 172.1 g of 98.7% pure 1-nitroanthraquinone (67.1% of the theoretical amount) are obtained as distillate.

EXAMPLE 4

208 g of anthraquinone are introduced into 1208 g of 99% nitric acid at 0° with stirring (mole ratio 19:1). After a reaction time of 110 minutes at 0°, the temperature is rapidly reduced to −20° to stop the reaction. 1797 g of 63.8% nitric acid (crystallisation acid 77%, $\gamma_{HNO_3} = 0.483$) are then slowly added for crystallisation. When the crystallised product has been filtered, it is washed with a little 70% nitric acid, freed from nitric acid and subjected to vacuum rectification at 5 Torr and a head temperature of 262°. 176.3 g of 99% 1-nitroanthraquinone are obtained (69% of the theoretical amount).

EXAMPLE 5

A mixture of 208 g of anthraquinone and 382 g of 99% nitric acid (mole ratio 6:1) is heated to 75° C for 10 hours with stirring and then slowly cooled to −10° ($\gamma_{HNO_3} = 0.695$). The precipitated product is filtered off, washed with a little 75% nitric acid, freed from nitric acid adhering to it by evaporation under vacuum, and fractionally distilled at 6 Torr and 267° head temperature. 151.5 g of 98.5% pure 1-nitroanthraquinone are obtained (59% of the theoretical amount).

EXAMPLE 6

208 g of anthraquinone are introduced with stirring into 99% nitric acid which is at a temperature of 45° (955 g, mole ratio 15:1). The isothermal reaction is then stopped after 9 minutes by rapid addition of 100 ml of water. Crystallisation is then brought about by slowly adding a further 105 ml of water (crystallisation acid 79%, $\gamma_{HNO_3} = 0.500$). The crystallisate is separated, washed with a little 75% nitric acid, freed from nitric acid adhering to it under a vacuum and fractionally distilled under a vacuum (5 Torr, head temperature 265°). 160.4 g of 99.4% pure 1-nitroanthraquinone are obtained (63% of the theoretical amount).

EXAMPLE 7

A mixture of 2.08 kg of anthraquinone and 9.545 kg of 99% nitric acid per hour (mole ratio 15:1) is cooled to 0° and continuously reacted in a flow tube reactor with a residence time of 13 minutes and a final temperature of 55°. The solution leaving the reactor is continuously cooled to −10° to stop the reaction and introduced into a crystallising apparatus together with 19.33 kg per hour of 66.2% nitric acid (crystallisation acid 76%, $\gamma_{HNO_3} = 0.469$). The precipitated product is continuously suction-filtered, washed with a little 76% nitric acid, freed from nitric acid adhering to it and subjected to continuous vacuum rectification (10 Torr, head temperature 281°). 1.740 kg of 98.9% pure 1-nitroanthraquinone are obtained per hour (68% of the theoretical amount).

EXAMPLE 8

208 g of anthraquinone are introduced into 764 g of 99% nitric acid (mole ratio 12:1) at room temperature with stirring. The reaction is then left to proceed adiabatically until the temperature reaches 45°. The reaction is then continued isothermally at 45° until the total reaction time is 17 minutes. The reaction is stopped by distilling off 330 g of 99% nitric acid. 128.0 g of 50% nitric acid (crystallisation acid 83.4%, $\gamma_{HNO_3} = 0.542$) are slowly added to the sump product (acid concentration approximately 94.4%, $\gamma_{HNO_3} = 0.725$). The product which precipitates under these conditions is suction-filtered, washed with a little dilute nitric acid, freed from nitric acid by washing with water, dried and subjected to vacuum rectification at 8 Torr with a head temperature of 275°. 162.3 g of 98.2% 1-nitroanthraquinone are obtained as a distillate (63% of the theoretical amount).

EXAMPLE 9

208 g of anthraquinone are introduced into 1145 g of 99% nitric acid (mole ratio 18:1) at 25° with cooling and the reaction mixture is stirred for 25 minutes. The reaction is then stopped by rapidly distilling off 693 g of 99% nitric acid and the product is precipitated by slowly cooling the reaction mixture to 0°. After washing with dilute nitric acid, the product is freed from nitric acid and distilled together with 800 g of paraffin oil at 30 Torr with a head temperature of between 250° and 300°. 1-Nitroanthraquinone which precipitates from the condensate is filtered off and freed from paraffin oil by washing with petroleum ether. 163 g of 98.9% pure 1-nitroanthraquinone are obtained (63.5% of the theoretical amount).

EXAMPLE 10

208 g of anthraquinone in 969 g of 97.5% nitric acid (mole ratio 15:1) are heated to 35° for 2 hours with stirring. The reaction is stopped by the addition of 103 ml of water. After removal of 265 g of 99% nitric acid by distillation (crystallisation acid 81%, $\gamma_{HNO_3}$ = 0.520), the precipitated product is freed from nitric acid and dried and distilled at 30 Torr with head temperatures of 250° to 300°, together with about 800 g of silicone oil. The yield of 99.2% 1-nitroanthraquinone is 153 g (60% of the theoretical amount).

EXAMPLE 11

208 g of anthraquinone are introduced into 955 g of 99% nitric acid (mole ratio 15:1) with stirring at room temperature without cooling. When a temperature of 55° is reached, the reaction is continued isothermally until the total reaction time is about 9 minutes. The reaction is then stopped by rapid removal of 376 g of 99% nitric acid by distillation (95.5% nitric acid, $\gamma_{HNO_3}$ = 0.779). Crystallisation is then started by slowly adding 1147 g of 70% nitric acid (crystallisation acid 78.1%, $\gamma_{HNO_3}$ = 0.492). The precipitated product is filtered off, briefly washed with dilute nitric acid, freed from nitric acid adhering to it by evaporation under vacuum and then fractionally distilled at 7 Torr with a head temperature of 275° C. 169.5 g of 98.5% pure 1-nitroanthraquinone (66% of the theoretical amount) are obtained.

What is claimed is:

1. Process for preparing 1-nitroanthraquinone substantially free from dinitroanthraquinone, which comprises:
   i. nitrating anthraquinone or a mixture which contains anthraquinone with at least 90% nitric acid at a temperature of at least 0° C wherein the mole ratio of nitric acid to anthraquinone is less than 20 to 1;
   ii. stopping the reaction when the anthraquinone conversion is at least 50% by cooling the reaction mixture to a temperature of at most 30° C and/or by adjusting the mole fraction of nitric acid in the reaction mixture to a value of at most 0.86;
   iii. precipitating 1-nitroanthraquinone by adjusting the mole fraction of nitric acid to a value of from 0.7 to 0.4 and/or by reducing the temperature to at most 20° C; and
   iv. separating the precipitated 1-nitroanthraquinone and subjecting it to vacuum distillation.

2. Process of claim 1 wherein 95 to 100% nitric acid is used for nitration.

3. Process of claim 1 wherein nitration is carried out with a mole ratio of nitric acid to anthraquinone of from 6:1 to 15:1.

4. Process of claim 1 wherein nitration is carried out at a temperature of at least 45° C.

5. Process of claim 4 wherein the temperature is from 55° to 75° C.

6. Process of claim 1 wherein the reaction is stopped after an anthraquinone conversion of from 80 to 100%.

7. Process of claim 1 wherein reduction of the nitric acid mole fraction to terminate the reaction is carried out by distilling off nitric acid.

8. Process of claim 1 wherein reduction of the nitric acid mole fraction to terminate the reaction is carried out by the addition of water.

9. Process of claim 1 wherein reduction of the nitric acid mole fraction by the addition of water and/or removal of nitric acid by distillation and/or reduction of the temperature to terminate the reaction is carried out in any sequence.

10. Process of claim 1 wherein reduction of the nitric acid mole fraction to precipitate 1-nitroanthraquinone is carried out by distilling off nitric acid.

11. Process of claim 1 wherein reduction of the nitric acid mole fraction to precipitate 1-nitroanthraquinone is carried out by the addition of water.

12. Process of claim 1 wherein reduction of the nitric acid mole fraction to precipitate 1-nitroanthraquinone is carried out by the addition of dilute nitric acid.

13. Process of claim 1 wherein reduction of the nitric acid mole fraction by the addition of dilute nitric acid and/or addition of water and/or removal of nitric acid by distillation and/or reduction of temperature is carried out in any sequence.

14. Process of claim 1 wherein 1-nitroanthraquinone which is precipitated from nitric acid and isolated is freed from nitric acid by drying.

15. Process of claim 14 wherein drying is carried out by vacuum drying.

16. Process of claim 1 wherein the reaction product is rectified together with the least one solvent which is inert under the conditions of rectification, and the crystallized 1-nitroanthraquinone is separated from the condensate.

17. Process of claim 16 wherein solvent boils at a temperature of from 100° to 350° C and the mixture is rectified at a temperature of from 200° to 350° C under a pressure of from 0.5 to 100 Torr.

18. Process of claim 16 wherein the solvent is a hydrocarbon.

19. Process of claim 16 wherein the solvent is a silicone.

* * * * *

UNITED STATES PATENT AND TRADEMARK OFFICE
CERTIFICATE OF CORRECTION

PATENT NO. : 4,031,116
DATED : June 21, 1977
INVENTOR(S) : Karl-Werner Thiem et al It is certified that error appears in the above-identified patent and that said Letters Patent are hereby corrected as shown below:

[57] Title Page, Abstract "20°C" should read -- 30°C --.

Column 3, line 18, "$\frac{n}{-}N_2$" should read -- $\frac{n}{-}N$ --.

Column 3, line 18, "$\frac{n}{-}H\,O$" should read -- $\frac{n}{-}H_2O$ --.

Column 4, line 34, "temperature" should read -- temperatures --.

Column 4, line 44, "$\gamma HNO$" should read -- $\gamma HNO_3$ --.

Column 7, line 37, "(more)" should read -- (mole) --.

Column 2, line 45, "Offenlegungschrift" should read -- Offenlegungsschrift --.

Signed and Sealed this

Eleventh Day of April 1978

[SEAL]

Attest:

RUTH C. MASON
*Attesting Officer*

LUTRELLE F. PARKER
*Acting Commissioner of Patents and Trademarks*